(12) United States Patent
Boissonneault

(10) Patent No.: US 7,704,984 B2
(45) Date of Patent: Apr. 27, 2010

(54) EXTENDED ESTROGEN DOSING CONTRACEPTIVE REGIMEN

(75) Inventor: Roger M. Boissonneault, Long Valley, NJ (US)

(73) Assignee: Warner Chilcott Company, LLC, Fajardo, PR (US)

(*) Notice: Subject to any disclaimer, the term of this patent is extended or adjusted under 35 U.S.C. 154(b) by 1382 days.

(21) Appl. No.: 11/112,290

(22) Filed: Apr. 22, 2005

(65) Prior Publication Data

US 2006/0241091 A1    Oct. 26, 2006

(51) Int. Cl.
*A61K 31/56* (2006.01)
*A61K 31/58* (2006.01)

(52) U.S. Cl. ........................... 514/170; 514/843
(58) Field of Classification Search ............ 514/170, 514/843
See application file for complete search history.

(56) References Cited

U.S. PATENT DOCUMENTS

| | | | |
|---|---|---|---|
| 4,921,843 | A | 5/1990 | Pasquale |
| 4,962,098 | A | 10/1990 | Boissonneault |
| 5,010,070 | A | 4/1991 | Boissonneault |
| 5,280,023 | A | 1/1994 | Ehrlich et al. |
| 5,510,341 | A | 4/1996 | Ehrlich et al. |
| 5,552,394 | A | 9/1996 | Hodgen |
| 5,747,480 | A | 5/1998 | Gast |
| 5,756,490 | A | 5/1998 | Lachnit et al. |
| 5,888,543 | A | 3/1999 | Gast |
| 5,898,032 | A | 4/1999 | Hodgen |
| 6,027,749 | A | 2/2000 | Schmidt-Gollwitzer et al. |
| 6,479,475 | B1 | 11/2002 | Gast |
| 2004/0176336 | A1* | 9/2004 | Rodriguez ............ 514/170 |

FOREIGN PATENT DOCUMENTS

WO    WO 98/04268    *  2/1998
WO    WO 2006/115871 A1    11/2006

OTHER PUBLICATIONS

Loose-Mitchell and Stancel, Chapter 58—Estrogen and Progestins, "Goodman & Gilman's The Pharmacological Basis of Therapeutics, 10th ed." Hardman JG, Limbird LE, and Gilman AG, Eds., McGraw-Hill, 2001, 1597-1634 (pp. 1597, 1618, 1623, and 1624 provided).* van De Waterbeemd H, Smith DA, Beaumont K, and Walker DK, "Property-based design: optimization of drug absorption and pharmacokinetics," Journal of Medicinal Chemistry, Apr. 2001,44(9), 1313-1333.*

Hillman Rs, Chapter 54 Hematopoietic Agents Growth Factors, Minerals, and Vitamins, "Goodman & Gilman's the Pharmacological Basis of Therapeutics, 10th ed." Hardman Jg, Limbird Lb, and Gilman Ag, Eds., McGraw-Hill, 2001, 1487-1518 (pp. 1487, 1495, and 1499 provided).*

Mircette Study Group,"An open-label, multicenter, noncomparative safety and efficacy study of Micette™, a low dose estrogen-progestin oral contraceptive"; *American Journal of Obstetrics and Gynecology*, Jul. 1998, vol. 179, No. 1, p. S2-S8.

Gaspard, U. et al., "New Forms of Hormonal Contraception"; *Journal de Gynécologie, Obstétrique et Biologie de al Reproduction*, May 2000, vol. 29, No. 3, p. 288-291.

European Patent Office, International Search Report for PCT/US2006/014367, Aug. 25, 2006.

* cited by examiner

*Primary Examiner*—Brandon J Fetterolf
*Assistant Examiner*—Paul Zarek
(74) *Attorney, Agent, or Firm*—Fitzpatrick, Cella, Harper and Scinto

(57) ABSTRACT

A method of contraception that provides for sequentially administering to a female of child bearing age: (a) a first composition containing a progestin in an amount equivalent to about 0.3 to about 1.5 mg norethindrone acetate and an estrogen in an amount equivalent to about 5 to about 20 mcg of ethinyl estradiol for about 22 to about 26 days; (b) a second composition containing an estrogen in an amount equivalent to about 5 to about 20 mcg of ethinyl estradiol for about 2 to about 3 days and an optional third composition that is a placebo provided that (i) if estrogen administration is continuous then the first composition is administered for 25 to 26 days, the second composition is administered for 2 to 3 days and no third composition is administered and (ii) if estrogen administration is not continuous then the first composition is administered for 22 to 24 days, the second composition is administered for 2 to 3 days and the third composition is administered for 1 to 4 days. The total cycle length is 28 days, with the first composition administered on day 1 of the menstrual cycle, defined as the first day of menstrual bleeding, or on the first Sunday after the first day of the menstrual cycle.

9 Claims, No Drawings

EXTENDED ESTROGEN DOSING CONTRACEPTIVE REGIMEN

BACKGROUND OF THE INVENTION

1. Field of the Invention

This invention is directed to an estrogenic/progestogenic contraceptive regimen with continuous and/or extended dosing of the estrogenic component. The inventive regimen provides for low daily estrogenic hormone exposure without compromising contraceptive efficacy or cycle control. A contraceptive kit that may be used to practice the method of the invention is also disclosed.

2. Related Background Art

Contraceptive compositions containing both estrogenic and progestogenic compounds are known to be effective in controlling ovulation and conception. The progestogenic component of the composition is primarily responsible for the contraceptive efficacy of the composition, while the estrogenic component is included primarily to reduce undesired side effects, such as breakthrough bleeding or spotting. It is thought that small amounts of estrogen help stabilize the endometrium and allow cyclic withdrawal bleeding, similar to the natural menstrual cycle.

The earliest of these estrogenic/progestogenic contraceptive compositions was administered monophasically (fixed dose) and contained a relatively high level of estrogenic component. U.S. Pat. No. 4,921,843 relates to the administration of an estrogen-only component from day 2 to day 7 of the menstrual cycle, followed by administration of a combination of estrogen and progestin from day 7 to day 28 of the menstrual cycle. U.S. Pat. No. 5,280,023 and U.S. Pat. No. 5,510,341 describe the administration of an estrogen-only component for 5 to 14 days at the beginning of the cycle, followed by 23 to 14 days of an estrogen/gestagen combination. U.S. Pat. No. 5,756,490 discloses combination preparations with 23 or 24 daily units of an estrogen and gestagen, and 4 to 10 daily units of estrogen only. Similarly, U.S. Pat. No. 6,027,749 discloses an estrogen-only component administered for 5, 6, or 7 days. U.S. Pat. No. 5,552,394 discloses administration of tablets that contain both estrogen and progestin for 24 days followed by 4 days of placebo.

U.S. Pat. No. 4,962,098 is directed to a multiphasic contraceptive regimen and describes a triphasic method of contraception using a progestin/estrogen combination in which the amount of estrogen is increased stepwise over the three phases wherein the first phase is 4-7 days, the second phase is 5-8 days and the third phase is 7-12 days. Preferably, administration of the contraceptive compositions for the three phases combined will be 21 days followed by a 7 day placebo period. For all three phases, the progestin is 0.5 to 1.5 mg of norethindrone acetate, while about 10 to 30 mcg of ethinyl estradiol is used in the first phase, about 20 to 40 mcg of ethinyl estradiol is used in the second phase and 30 to 50 mcg of ethinyl estradiol is employed in the third phase.

U.S. Pat. No. 5,747,480 also discloses a multiphasic regimen wherein the progestin component is levonorgestrel. U.S. Pat. No. 5,888,543 discloses various regimens wherein a combination of progestin and estrogen are administered in a monophasic or multiphasic regimen (varied dose, e.g., biphasic or triphasic). In one embodiment, a combination of a progestin composition and an estrogen composition is administered such that the daily dosage of the second phase progestin is greater than the daily dosage of progestin in the first phase and the daily dosage of the second phase estrogen is greater than or equal to the daily dosage of estrogen in the first phase. U.S. Pat. No. 6,479,475 describes multiphasic regimens with 23-25 consecutive days of hormone administration, followed by a 3-5 day hormone-free interval.

U.S. Pat. No. 5,898,032 discloses an extended oral contraceptive regimen wherein estrogen and progestin are administered in a combined dosage form, preferably monophasically, for 60 to 110 consecutive days, followed by an administration free period of 3 to 10 days. The amount of estrogen and progestin administered daily are equivalent to about 5-35 mcg of ethinyl estradiol and about 0.025 to 10 mg of norethindrone acetate, respectively. In one particular embodiment, the combined dosage form is administered for 84 days followed by 7 pill free days. Following this particular regimen is said to result in four treatments and menstrual cycles during the year. However, extended oral contraceptive regimens tend to suffer from poor initial cycle control. Another disadvantage is that once breakthrough bleeding is under control, the user becomes functionally amenorrheic. This does not reassure the user that she is not pregnant.

One constant goal in the oral contraceptive art has been to reduce the hormone levels of such compositions without reducing contraceptive efficacy and increasing undesired side effects. Since the risk is acute thrombosis (as opposed to atherosclerosis), minimizing daily exposure of estrogen is a therapeutic goal. However, as estrogen doses decreased, the incidences of unwanted breakthrough bleeding or spotting have generally increased. Therefore, there remains a need for an oral contraceptive regimen that maintains contraceptive efficacy and provides adequate cycle control with a low daily dose of the estrogenic component.

SUMMARY OF THE INVENTION

The present invention is directed to a method of contraception that comprises the steps of sequentially administering to a female of child-bearing age: (a) a first composition containing a progestin in an amount equivalent to about 0.3 to about 1.5 mg norethindrone acetate and an estrogen in an amount equivalent to about 5 to 20 mcg of ethinyl estradiol for about 22 to about 26 days; (b) a second composition containing an estrogen in an amount equivalent to about 5 to about 20 mcg of ethinyl estradiol and substantially free of a progestin for about 2 to about 3 days; and (c) an optional third composition that is a placebo, wherein the sequential administration of the first composition, the second composition and the optional third composition, when present, is performed on a daily basis over a 28 day cycle. If estrogen administration is continuous during the cycle then the first composition is monophasically administered for 25 to 26 days, the second composition is administered for 2 to 3 days and no third composition is administered, while if estrogen administration is extended, but not continuous, then the first composition is administered for 22 to 24 days, the second composition is administered for 2 to 3 days and the third composition is administered for 1 to 4 days. The sequential administration is begun on the first day of the female's menstrual cycle.

One particular embodiment of this invention is directed to a method of contraception that provides for sequentially administering to a female of child bearing age (a) a composition containing a progestin in an amount equivalent to about 0.3 to about 1.5 mg norethindrone acetate and an estrogen in an amount equivalent to about 5 to about 20 mcg of ethinyl estradiol for about 25 or about 26 days; and (b) a composition containing an estrogen in an amount equivalent to about 5 to about 20 mcg of ethinyl estradiol for about 3 to about 2 days for a total cycle length of 28 days. No placebo is administered in this embodiment. The sequential administration of the first composition may be repeated the day following the completion of the administration of the second composition to provide for continuous administration of estrogen.

Yet another embodiment of this invention is directed to a method of contraception that provides for sequentially administering to a female of childbearing age (a) a composition containing a progestin in an amount equivalent to about 0.3 to about 1.5 mg norethindrone acetate and an estrogen in an amount equivalent to about 5 to about 20 mcg ethinyl estradiol for about 22 to about 24 days; (b) a composition containing an estrogen in an amount equivalent to about 5 to about 20 mcg ethinyl estradiol for about 2 to 3 days; and (c) a placebo tablet for about 1 to about 4 days for a total cycle length of 28 days. This embodiment provides for extended, but not continuous, administration of estrogen. The sequential administration of the first composition may be repeated the day following the completion of the administration of the placebo to provide for continuous contraception.

In preferred embodiments of the invention, the amount of estrogenic component remains the same in both phases of administration, and the amount of progestin remains constant during the first phase of administration. The invention is also directed to a kit for practicing the method of this invention.

DETAILED DESCRIPTION OF THE INVENTION

By practicing the contraceptive method disclosed herein, a user advantageously improves control of menstrual bleeding while taking the contraceptive compositions of the invention. For the purposes of this invention, the designation "mcg" refers to micrograms and "mg" to milligrams.

In a preferred embodiment, the amount of estrogen administered is equivalent to 15 mcg per day of ethinyl estradiol, while the amount of progestin administered is equivalent to 1.0 mg norethindrone acetate per day during the combined estrogen/progestin phase.

The progestin may be selected, for example, from the group consisting of norethindrone acetate, drospirenone, trimegestone, norethindrone, levonorgestrel, desogestrel, 3-ketodesogestrel, gestodene, demogestone, dydrogesterone, medrogestone, medroxy progesterone, esters and mixtures thereof and the like. The most preferred progestin is norethindrone acetate. The estrogen may be selected, for example, from the group consisting of ethinyl estradiol, 17-β-estradiol, conjugated estrogens, mestranol, estrone and esters, prodrugs and salts thereof. An exemplary ester is estradiol acetate. Preferred salts of estrone include, but are not limited to the sodium and piperate salt. For the conjugated estrogens, 1.25 mg conjugated estrogens is equivalent to a daily dose of 15 mcg ethinyl estradiol. The most preferred estrogen is ethinyl estradiol. The amount of progestin and estrogen employed in each phase will be that amount which is equivalent in potency to the ranges of norethindrone acetate and ethinyl estradiol, respectively, that are set forth herein. Determination of equivalent potency is well understood and readily accomplished by those of ordinary skill in the art.

The third composition, if present is a placebo, i.e., a non-steroidal component. The non-steroidal placebo may comprise an iron supplement. Suitable iron supplements include, for example, ferrous fumarate, ferrous sulfate, ferrous gluconate, iron polysaccharides, and mixtures thereof. The preferred iron supplement is ferrous fumarate, most preferably a daily placebo dosage will be equivalent to not more than about 75 mg ferrous fumarate.

One goal of the extended estrogen dosing contraceptive regimen is to minimize daily exposure to estrogen from either exogenous or endogenous sources. Without wishing to be bound by theory, it is believed that continuous dosage of low amounts of estrogen may suppress FSH (follicle-stimulating hormone) and minimize follicular recruitment and therefore minimize estrogen contribution from the developing follicle. The cyclic addition of a progestin component suppresses both leutenizing hormone and ovulation while maintaining the integrity of the endometrium. Discontinuation of the progestin provides a withdrawal bleed.

The limitations of continuous low dose estrogen and progestin is irregular bleeding patterns due to a lack of an adequate withdrawal bleed. Although a higher dose 24-day regimen provides an adequate withdrawal bleed and fewer bleeding days, follicular suppression may not be optimal. The present invention provides in one embodiment that by extending the estrogen/progestin dosing beyond 24 days (e.g., 25-26 days) and utilizing estrogen alone for the rest of the cycle results in superior follicular suppression, less endogenous estrogen and therefore a more predictable withdrawal bleed of fewer days. Alternatively, in yet another embodiment dosing estrogen/progestin for 22-24 days and estrogen alone for 2-3 days with the addition of a placebo for the remainder of the cycle will allow follicular suppression while improving the reliability of a withdrawal bleed. These regimens allow for lower daily exposure to estrogen, while not compromising cycle control, and fewer days of cyclic withdrawal bleeding. If cyclic bleeding is predictable and a modest event, this natural episode provides reassurance to reproductive women that they are not pregnant and the extended cycle monophasic continuous dosing described in U.S. Pat. No. 5,898,032 provides little or no advantage.

The compositions used in this invention are administered using a suitable daily dosage form. Tablets, pills, capsules, and caplets are exemplary dosage forms. Suitable carriers with which the compositions can be administered include lactose, starch, cellulose derivatives and the like used in suitable amounts. Lactose is a preferred carrier. Mixtures of carriers, e.g. lactose, microcrystalline cellulose and starch, may also be used. In general, any pharmaceutically-acceptable additive which does not interfere with the function of the active components can be used in one or more of the compositions. These additives include conventional additives, e.g., fillers, colorants, polymeric binders, and the like.

The terms "method" and "kit" are used herein to encompass any drug delivery system via the use of which the invention outlined above can be effectively administered to human females. The contraceptive kit of this invention is a package containing the daily dosages of the compositions for practicing the method of this invention. Various types of packages for holding contraceptives are well known and it is contemplated that any such packaging may be used or altered for use in the practice of the present invention. For example, a single cycle package of the present invention for use in continuous estrogen dosing would preferably include about 25 to about 26 monophasic daily dosages of the first composition and about 2 to about 3 daily dosages of the second composition, with a total of 28 dosages. A single cycle package of the present invention for use in extended, but not continuous, estrogen dosing would preferably include about 22 to about 24 daily dosages of the first composition, about 2 to 3 daily dosages of the second composition and 1 to 4 daily dosages of the third composition, with a total of 28 dosages. The kit will also include instructions and/or indicia indicating that the first daily dosage of the first composition should be administered on the first day of the menstrual cycle, which is defined as the first day of menstrual bleeding, or on the first Sunday after the first day of the menstrual cycle.

EXAMPLES

The following examples are used to explain the invention in more detail. The dosage units are formulated conventionally using tablets, pills, coated tablets, and the like.

Example 1

Continuos Estrogen Contraceptive Regimen

| | Day | | | | | | |
|---|---|---|---|---|---|---|---|
| | 1 | 2 | 3 | 4 | 5 | 6 | 7 |
| Composition | C | C | C | C | C | C | C |

| | Day | | | | | | |
|---|---|---|---|---|---|---|---|
| | 8 | 9 | 10 | 11 | 12 | 13 | 14 |
| Composition | C | C | C | C | C | C | C |

| | Day | | | | | | |
|---|---|---|---|---|---|---|---|
| | 15 | 16 | 17 | 18 | 19 | 20 | 21 |
| Composition | C | C | C | C | C | C | C |

| | Day | | | | | | |
|---|---|---|---|---|---|---|---|
| | 22 | 23 | 24 | 25 | 26 | 27 | 28 |
| Composition | C | C | C | C | E | E | E |

Day 1 is first day of bleeding.
C = 1.0 milligrams Norethindrone Acetate and 15 micrograms Ethinyl Estradiol
E = 15 micrograms Ethinyl Estradiol

Example 2

Extended Estrogen Contraceptive Regimen

| | Day | | | | | | |
|---|---|---|---|---|---|---|---|
| | 1 | 2 | 3 | 4 | 5 | 6 | 7 |
| Composition | C | C | C | C | C | C | C |

| | Day | | | | | | |
|---|---|---|---|---|---|---|---|
| | 8 | 9 | 10 | 11 | 12 | 13 | 14 |
| Composition | C | C | C | C | C | C | C |

| | Day | | | | | | |
|---|---|---|---|---|---|---|---|
| | 15 | 16 | 17 | 18 | 19 | 20 | 21 |
| Composition | C | C | C | C | C | C | C |

| | Day | | | | | | |
|---|---|---|---|---|---|---|---|
| | 22 | 23 | 24 | 25 | 26 | 27 | 28 |
| Composition | C | C | C | E | E | P | P |

Day 1 is first day of bleeding.
C = 1.0 milligrams Norethindrone Acetate and 15 micrograms Ethinyl Estradiol
E = 15 micrograms Ethinyl Estradiol
P = Placebo While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A method of contraception comprising the steps of sequentially administering to a female of child-bearing age:
   (a) a first composition containing a progestin in an amount equivalent to about 0.3 to about 1.5 mg norethindrone acetate wherein the progestin is selected from norethindrone acetate or norethindrone and 5 to 15 mcg of ethinyl estradiol for 24 days;
   (b) a second composition containing 5 to 15 mcg of ethinyl estradiol and substantially free of a progestin for 2 days; and
   (c) a third composition that is a placebo,
   wherein the sequential administration of the first composition, the second composition and the third composition, is performed on a daily basis over a 28 day cycle.

2. The method according to claim 1, wherein the sequential administration is repeated beginning the day after completion of the 28 day cycle.

3. The method according to claim 1, wherein the progestin in the first composition is norethindrone acetate.

4. The method according to claim 3, wherein the amount of norethindrone acetate in the first composition is about 1 mg.

5. The method according to claim 1, wherein the placebo contains about 75 mg of ferrous fumarate.

6. The method according to claim 4, wherein the amount of ethinyl estradiol in the first and second composition is the same.

7. A method of contraception comprising the steps of sequentially administering to a female of child bearing age:
   (a) a first composition containing about 0.3 to about 1.5 mg norethindrone acetate and 5 to 15 mcg ethinyl estradiol for 24 days;
   (b) a second composition containing 5 to 15 mcg of ethinyl estradiol and substantially free of a progestin for 2 days;
   (c) a third composition that is a placebo for 2 days,
   wherein the sequential administration of the first composition, the second composition and the third composition is performed on a daily basis over a 28 day cycle.

8. The method according to claim 7, wherein the first composition contains about 1 mg of norethindrone acetate.

9. The method according to claim 7, wherein the amount of ethinyl estradiol in the first and second composition is the same.

* * * * *